(12) United States Patent
Krummel et al.

(10) Patent No.: US 7,795,586 B2
(45) Date of Patent: Sep. 14, 2010

(54) DEVICE FOR DETECTING AND DEVICE FOR MEASURING THE CONCENTRATION OF A SUBSTANCE

(75) Inventors: Christian Krummel, Kirchentellinsfurt (DE); Michael Arndt, Reutlingen (DE); Michael Saettler, Kusterdingen (DE); Frank Fischer, Gomaringen (DE)

(73) Assignee: Robert Bosch GmbH, Stuttgart (DE)

( * ) Notice: Subject to any disclaimer, the term of this patent is extended or adjusted under 35 U.S.C. 154(b) by 145 days.

(21) Appl. No.: 10/528,181

(22) PCT Filed: Feb. 27, 2003

(86) PCT No.: PCT/DE03/00631

§ 371 (c)(1), (2), (4) Date: Oct. 30, 2006

(87) PCT Pub. No.: WO2004/027397

PCT Pub. Date: Apr. 1, 2004

(65) Prior Publication Data

US 2007/0057187 A1   Mar. 15, 2007

(30) Foreign Application Priority Data

Sep. 17, 2002   (DE) .................. 102 43 014

(51) Int. Cl.
*G01J 5/00* (2006.01)
(52) U.S. Cl. .................. 250/339.1
(58) Field of Classification Search ............ 250/339.13
See application file for complete search history.

(56) References Cited

U.S. PATENT DOCUMENTS

| 5,426,412 | A | * | 6/1995 | Tomonari et al. ............ 338/18 |
| 5,721,430 | A |   | 2/1998 | Wong |
| 5,892,140 | A | * | 4/1999 | Wood ..................... 73/23.31 |
| 5,942,755 | A |   | 8/1999 | Dreyer |
| 6,106,735 | A | * | 8/2000 | Kurle et al. .................. 216/2 |
| 6,369,386 | B1 | * | 4/2002 | Charlier et al. ......... 250/338.1 |
| 2003/0154487 | A1 |   | 8/2003 | Tsumura |
| 2005/0178952 | A1 | * | 8/2005 | Wood ..................... 250/214 R |
| 2005/0179102 | A1 | * | 8/2005 | Weiblen et al. ............ 257/432 |

FOREIGN PATENT DOCUMENTS

| DE | 198 35 769 | 2/2000 |
| JP | 2001 228022 | 8/2001 |
| JP | 2002 71451 | 3/2002 |

OTHER PUBLICATIONS

Portnoff et al., *Enhancement of MOS Gas Sensor Selectivity by 'On-Chip' Catalytic Filtering*, Sensors and Actuators, Lausanne, Switzerland, Aug. 1, 1991, vol. B05, No. 1/4, pp. 231-235.

* cited by examiner

*Primary Examiner*—David P Porta
*Assistant Examiner*—Marcus H Taningco
(74) *Attorney, Agent, or Firm*—Kenyon & Kenyon LLP

(57) ABSTRACT

A device for detecting radiation signals and a device for measuring the concentration of a substance are described, a first detector and a second detector being provided on a first chip, and a first filter and a second filter being provided on a second chip, the first chip and the second chip being connected to one another in hermetically sealed fashion.

11 Claims, 1 Drawing Sheet

DEVICE FOR DETECTING AND DEVICE FOR MEASURING THE CONCENTRATION OF A SUBSTANCE

FIELD OF THE INVENTION

The present invention starts out from a device for detecting and a device for measuring the concentration of a substance.

BACKGROUND INFORMATION

Devices for detecting radiation signals are already known and are used, for example, for determining the concentration of a gas using infrared absorption. Interfering gases in a gas volume, for example, in the interior of a motor vehicle, are, for example, CO2, CO, H2O or also CH4, carbon dioxide CO2 originating, in particular, from the respired air of persons in the gas volume or also from CO2 air-conditioning systems. Such interfering gases are detected using generally known gas detectors. Such gas detectors are also used in the area of laboratory analysis, safety technology, the food industry, air-conditioning systems, building technology, medicine, the household, environmental protection, etc. Different sensor principles, whose use depends essentially on the sensitivity, are used to determine the concentration of such interfering gases. For example, there are chemical sensors in which the resistance of a chemically reactive layer changes when it comes into contact with specific gases. However, these sensors are very sensitive, even to gases other than those that are to be detected, or also to environmental effects. Furthermore, the long-term stability of such sensors is a problem. Another physical method makes use of the different thermal conductivities of, for example, CO2 and air, that is, essentially nitrogen, in order to draw conclusions concerning the carbon dioxide content in a gas volume, such as in the interior of a motor vehicle. Furthermore, it is known that the absorption of infrared light by gas molecules may be used to detect such gas molecules. If, namely, a gas molecule, which is made up of several identical or different atoms, is stimulated by infrared light, it is converted to higher energy states. For example, rotational or vibrational moments are stimulated, whose energy state is specific to the molecule. By stimulating the higher energy states, energy is withdrawn from the optical radiation; the characteristic absorption bands of gases typically are in the infrared range for wavelengths between 1 μm and 10 μm. This means that infrared light passing through such a gas-filled space increasingly loses total intensity, the attenuation being a function of the gases present and of their concentration. The intensity of the light in the wavelength region of the absorption bands of the respective gases can be determined by a spectrally resolved measurement of the intensity. It is thereby possible to break down even mixtures of several gases with a high degree of resolution. An instrument for determining the gas concentration by infrared absorption according to the related art is shown in FIG. 1 and typically includes an infrared light source 20, a cuvette 30 or a tube 30, which is filled with the gas mixture to be analyzed and carries the light beam, and one or more filters 41, 42 which bring about the spectral dispersion of the infrared light, one or more detectors 51, 52 with which the intensity of the thermal radiation is measured after the spectral dispersion being provided behind filters 41, 42. However, such known devices have the disadvantage that they are expensive systems.

SUMMARY OF THE INVENTION

In comparison, the device of the present invention has the advantage that a cost-effective device for detecting radiation signals and a cost-effective device for measuring the concentration of a substance are possible. Furthermore, it is advantageous that the device exhibits greater leak tightness between the filter and the detector. Furthermore, it is advantageous pursuant to the invention that a simple construction and connection technique is employed, which, in turn, lowers the costs. The inventive device has no moving parts, so that it is able to withstand being dropped and has a high overload resistance. Due to the hermetic connection between detector and filter, a narrow specification for filter tolerances can be ensured. Furthermore, pursuant to the invention, the device may be made very small, resulting, in turn, in cost advantages as well as in installation advantages. According to the present invention, it is possible and intended to develop a plurality of filters for two to more than six gases jointly and combined with one another. Such an integration of filter arrays according to the invention is therefore possible in a cost-effective and simple manner.

It is particularly advantageous that the detectors are provided as thermopiles, temperature-sensitive resistors or temperature-sensitive diodes. It is thus possible to resort to cost-effective and proven components as detectors. Furthermore, it is of advantage that an absorber layer is provided on at least one of the detectors. The effectiveness and sensitivity of the detector may thereby be increased. Furthermore, it is of advantage that the first chip includes a first substrate, the first and second detectors being thermally decoupled from the first substrate. According to the present invention, it is thereby possible for the inventive device to be particularly insensitive to external disturbance variables such as the ambient temperature. Furthermore, it is of advantage that the first and/or second filter is a Fabry-Perot filter. As a result, it is possible to provide a narrow-band filter particularly simply and cost-effectively.

DETAILED DESCRIPTION

Figure 1:
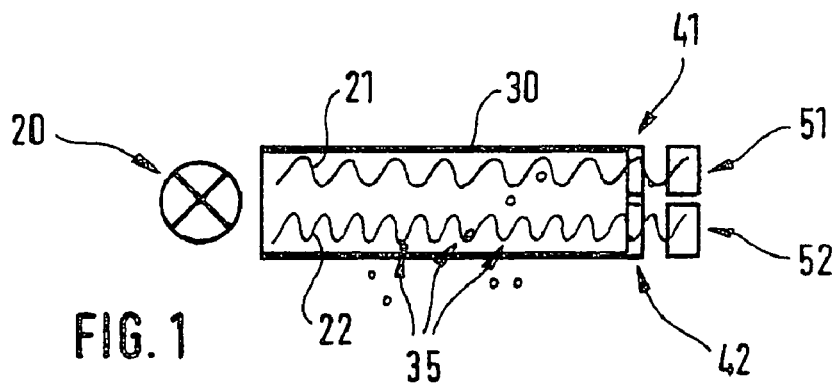
FIG. 1 shows a system according to the related art for measuring the gas concentration.

FIG. 1 shows the system already described for detecting a gas concentration. In tube 30 or in cuvette 30 are, first of all, the beam paths or beam courses of the infrared radiation which are labeled 21 and 22 and start out from light source 20, and gas molecules 35 to be detected. The radiation, which starts out from radiation source 20, has been attenuated at filters 51, 52 by the gas molecules in certain wavelength regions. The decrease in the intensity of the light by the infrared absorption is measured in gas-specific wavelength regions. First filter 41, which permits only narrow-band transmission, is used to separate the wavelength regions of interest. The transmitted radiation is then measured downstream of filter 41 by a wavelength-unspecific detector 51. In order to draw conclusions concerning the gas concentration, the infrared intensity in the area of the absorption bands—via the filter and detector 41, 51—is compared with the intensity of the lamp in a reference region—second filter and detector 42, 52—in which there is no significant infrared absorption by relevant gases. For this purpose, further filter 42, which permits passage of a defined reference spectrum, and corresponding detector 52 are required.

Figure 2:
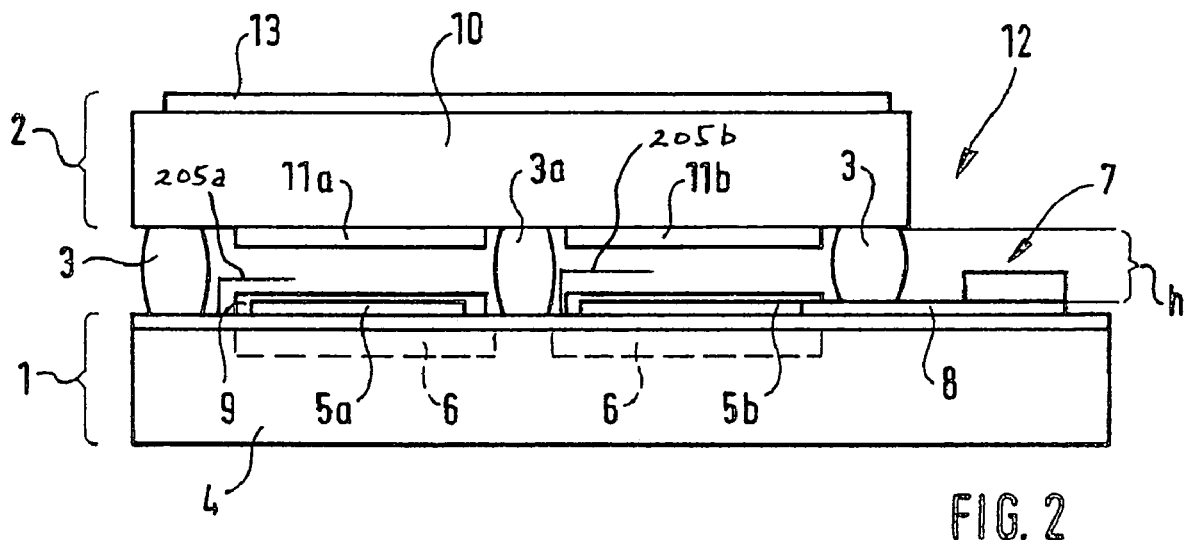
FIG. 2 shows a device according to the present invention for detecting radiation signals.

In FIG. 2, the fundamental construction of a device of the present invention for detecting radiation signals, i.e. the sensor of the present invention, is shown diagrammatically. Pursuant to the invention, the sensor has a detector chip 1 and a filter chip 2, filter chip 2 being applied on detector chip 1 by a wafer-bonding method via connecting webs 3. In the following, detector chip 1 is also referred to as first chip 1 and includes a first substrate 4, which is provided particularly as silicon substrate 4. A first temperature sensor 5a and a second temperature sensor 5b are disposed as first detector 5a and second detector 5b on first substrate 4. Pursuant to the invention, it is entirely possible that further temperature sensors, which are, however, not shown in FIG. 2, are disposed on first substrate 4. Temperature sensors 5a, 5b, i.e. detectors 5a, 5b may be provided, for example, as thermopiles, as temperature-sensitive resistors or as temperature-sensitive diodes. Pursuant to the invention, an absorber layer may be applied on first detector 5a and/or second detector 5b. In FIG. 2, this absorber layer for first detector 5a is marked by reference number 9. Absorber layer 9 is suitable for absorbing long wavelength infrared radiation. Pursuant to the invention, the absorber is stable at temperatures used in the bonding method, employed pursuant to the invention, between first chip 1 and second chip 2. In the present invention, the following materials are used as absorber layer:

Stable polymers, doped glasses, sequences of dielectric layers, highly doped semiconductors, narrow-band semiconductors, metals, etc. Pursuant to the invention, thermal decoupling is furthermore provided between detectors 5a, 5b and first substrate 4. For this purpose, a cavity, for example, is provided between detectors 5a, 5b and first substrate 4, as indicated in FIG. 2 by reference numeral 6. A surface micromechanical technique is employed, for instance, to produce such a cavity 6 or such a cavern 6. For such techniques, porous silicon is used in partial regions of first substrate 4. Subsequently, the porous silicon is rearranged in such a manner that a lower region is provided, which forms a cavity, and that a higher region is provided, which forms a covering layer for first substrate 4 for accommodating detectors 5a, 5b. Furthermore, it is possible to produce such a cavity 6 using a known etching by xenon difluoride, ClF3, ClF5, by other interhalogen compounds which are able to etch substrate 4 isotropically, or by plasma-activated NF3. In addition to detectors 5a, 5b, heating conductors 205a, 205b are also provided, pursuant to the invention, in the area of detectors 5a, 5b as shown in FIG. 2. Such a heating conductor is provided in the inventive device for self-testing the sensor or the device. According to the present invention, a brief thermal pulse is produced by way of the heating conductor on the thermally decoupled area of detectors 5a, 5b. The function of temperature sensors 5a, 5b may thereby be tested.

Terminals of temperature sensors 5a, 5b are connected to bonding pads 7 via conductor tracks provided with reference numeral 8 in FIG. 2. Conductor tracks 8 should have a small topographic width of less than 5 µm, so that bonding connection 3 between first chip 1 and second chip 2 ensures a hermetic inclusion of filigrained temperature sensors 5a, 5b. Pursuant to the invention, temperature sensors 5a, 5b may also be separated from one another by bonding webs. Such a bonding web is labeled 3a in FIG. 2. Temperature sensors 5a, 5b may be separated better and decoupled better by such separating bonding webs 3a. Height h of bonding webs 3, 3a is such that temperature sensors 5a, 5b are unable to come into mechanical contact with the filter layers, which are labeled 11a, 11b in FIG. 2. Pursuant to the invention, a height h of 3 µm to 12 µm is sufficient for bonding webs 3, 3a. However, this value is not of major importance for the functionality of the sensor or of the device.

Filter chip 2, also referred to in the following as second chip 2, includes a carrier 10, the latter being provided, for example, as a silicon substrate or also as a glass substrate. On the underside of carrier 10, also referred to in the following as second substrate 10, Fabry-Perot filters 11a and 11b are provided. They are also referred to in the following as first filter 11a and second filter 11b. According to the invention, first filter 11a is used to filter the reference wavelength and second filter b is used to filter the analysis wavelength. In the following, the analysis wavelength is also referred to as absorption bands. Pursuant to the invention, filters 11a, 11b are provided, in particular, as a monolayer system, for example, made of silicon dioxide or silicon nitride. They may also be constructed as multilayers. Pursuant to the invention, first filter 11a is designed for a reference wavelength. Second filter 11b is provided for the analysis wavelength in the region of the absorption bands of the gas to be detected. Filters 11a, 11b must therefore differ from one another and accordingly must be locally patterned and produced separately from one another. In filter chip 2 or second chip 2, which is to act as a cap for first chip 1 or detector chip 1, recesses 12 are etched, through which bonding wires, which are not shown in FIG. 2, may be passed to metal contacts 7 or bonding pads 7. In producing through hole 12, care must be taken that filter structures 11a, 11b are not etched.

A bonding method is used to connect cap chip 2 or second chip 2 to detector chip 1, anodic bonding, seal-glass bonding, polymer bonding, eutectic bonding, laser transmission welding or a different method being used here pursuant to the invention. Such bonding methods usually are carried out at temperatures of 150° C. to about 500° C. For this reason, it is necessary that the materials of filter structures 11a, 11b involved, of detectors structures 5a, 5b involved and of absorber layer 9 are not decomposed at these temperatures. Pursuant to the invention, a capping method preferably is used, in which a vacuum can be produced underneath second chip 2. It is thereby possible, pursuant to the invention, to bring about or increase a thermal decoupling of detectors 5a, 5b from the surroundings. Pursuant to the invention, chip 1 is capped with second chip 2 especially at the wafer level, that is, a plurality of second chips 2 are printed in the form of a cap wafer with filters 11a, 11b applied thereon, for example, with a seal glass (in the case of seal glass bonding), subsequently annealed and bonded on a plurality of first chips 1, which jointly form the detector wafer. Subsequently, the entire arrangement of filter and detector may be tested electrically and possibly also electrooptically on the wafer level. Only subsequently are the individual devices of the present invention, for which first chip 1 is connected to second chip 2, sawn and separated using known methods.

For detecting gases, the light source, which is given reference number 20 in FIG. 1 and with which the broad-band infrared radiation is generated, may be operated in pulsed fashion. This is advantageous if the thermal decoupling of sensors 5a, 5b by cavity 6 or cavern 6 is inadequate and there is significant heating of the surroundings of sensors 5a, 5b during continuous operation. A further inventive possibility to counter such a disadvantageous heating of the surroundings of sensors 5a, 5b is to mount on the side of second chip 2 opposite filter layers 11a, 11b, pass filters, labeled 13 in FIG. 2, which cut off wavelengths between the absorption edge of the material of the second chip, that is, essentially the material of second substrate 10 and the reference or detection wavelengths. Instead of pass filter 13, an anti-reflection layer may also be provided pursuant to the invention. According to the present invention, this antireflection layer may also be provided in addition to pass filter 13. When silicon is used as second substrate 10, the absorption edge corresponds, for example, to a wavelength of about 1 μm. Mounting pass filter 13 pursuant to the invention prevents higher filter orders from playing a role during the measurement. Pass filter 13 may also be integrated in the packaging of the sensor element. Pursuant to the invention, layer 13 is made in particular of a polymer, a semiconductor, a dielectric multilayer or the like.

According to the present invention, a novel, cost-effective sensor or an inventive device is made available, with which the light intensity, resolved spectrally, may be measured in a simple way. Pursuant to the invention, such sensors or devices are to be used for determining the composition of mixtures of two or more gases. Filters 11a, 11b, as well as detectors 5a, 5b of the inventive device are produced by methods of silicon micromechanics. The device is one in which filters 11a, 11b and detectors 5a, 5b are provided integrated in a single device. The first chip or also detector chip 1 is produced completely by surface micromechanics. Detector structure 5a, 5b is subsequently capped. Pursuant to the invention, discrete static filters are provided in the cap and are placed for filtering the absorption and reference bands over detector structures 5a, 5b. Particularly on the upper side of the second chip, the device of the present invention may include further pass-filter layers 13, which suppress higher orders of the Fabry-Perot filters or of filters 11a, 11, which leads to an absorption at shorter wavelengths. In comparison to previously known devices, the device or sensor of the present invention has several decisive advantages, particularly relating to cost-effective producibility by batch processing using silicon micromechanics, to a comparatively simple construction or to a simple construction and connecting technique and to the possibility of integrating several filter arrays for 2 to more than 6 gases.

Figure 3:
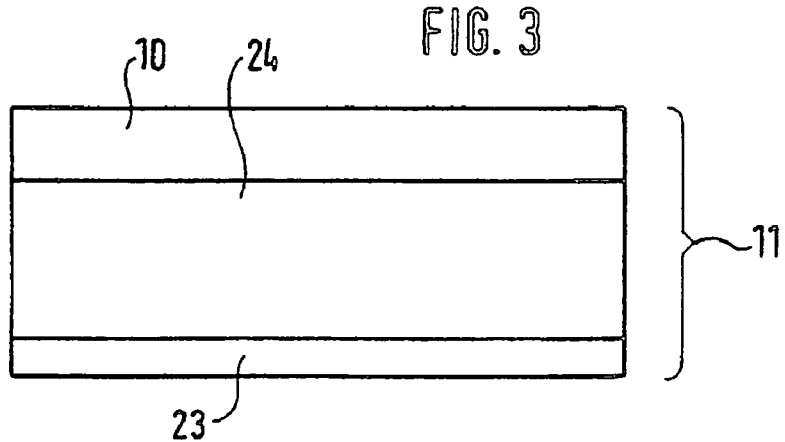
FIG. 3 shows a known Fabry-Perot filter.

In FIG. 3, the construction of a Fabry-Perot filter is shown schematically. Such a structure, as a whole, is labeled 11. A structure of this type may be used in the device of the present invention. In principle, a Fabry-Perot filter 11 is made of two plane-parallel mirrors, between which there is a medium 24, which determines the optical path and, with that, the central wavelength of the pass filter function. The thickness and the refractive index of filter cavity 24 or of medium 24 determine the average filter wavelength. The reference wavelength and the analysis wavelength of the device are adjusted by the design of this medium 24 or of this filter cavity 24, namely, by whether it is a monolayer or a multilayer, by its layer thickness and its refractive index. The two mirrors of Fabry-Perot filter 11 are produced, for example, by a jump in the refractive index between the material of medium 24 and the material of second substrate 10 or between the material of medium 24 and the material of covering layer 23. In order to sharpen the filter characteristics of Fabry-Perot filter 11, second substrate 10 and covering layer 23 may also be produced from multilayers or from semi-transparent metal layers. Pursuant to the invention, covering layer 23 is made from a material which is resistant to the processes for cap patterning, such as KOH etching or the like, or to processes for patterning dielectric layers during filter production, such as HF etching. Pursuant to the invention, the use of a layer sandwich for producing filters 11a, 11b is preferred for first filter 11a, and for second filter 11b, polysilicon, silicon dioxide and/or silicon nitride being selected as material for covering layer 23. The width of the filter function is determined by the degree of reflectivity of the mirrors.

What is claimed is:

1. A device for measuring a concentration of a substance in a beam path of a radiation source, comprising:
   a first detector;
   a second detector;
   a first chip on which are arranged the first detector and the second detector;
   a first filter;
   a second filter; and
   a second chip on which are arranged the first filter and the second filter; wherein:
      the first chip and the second chip are connected to one another in a hermetically sealed fashion, at least one hermetically sealed region being vertically interposed between the first chip and the second chip; and
      a hermetic seal between the first and second chips includes a bonding web connecting the first and second chips.

2. The device as recited in claim 1, wherein:
   each of the first detector and the second detector includes one of a thermopile, a temperature-sensitive resistor, and a temperature-sensitive diode.

3. The device as recited in claim 1, further comprising:
   an absorber layer provided on at least one of the first detector and the second detector.

4. The device as recited in claim 1, wherein:
   the first chip includes a first substrate, and
   the first detector and the second detector are thermally decoupled from the first substrate.

5. The device as recited in claim 1, wherein:
   at least one of the first filter and the second filter includes a Fabry-Perot filter.

6. The device as recited in claim 1, further comprising:
   at least one further detector; and
   at least one further filter.

7. The device as recited in claim 1, further comprising:
   a self-test mechanism for the device, wherein the self-test mechanism includes at least one heating conductor configured to apply heat to at least one of the first and second detectors.

8. A device for measuring a concentration of a substance in a beam path of a radiation source, comprising:
   a first detector;
   a second detector;
   a first chip on which are arranged the first detector and the second detector;
   a first filter;
   a second filter; and
   a second chip on which are arranged the first filter and the second filter; wherein:
      the first chip and the second chip are connected to one another in a hermetically sealed fashion; and
      the first detector and the second detector are hermetically isolated from each other.

9. The device as recited in claim 8, further comprising:
   a self-test mechanism for the device, wherein the self-test mechanism includes at least one heating conductor configured to apply heat to at least one of the first and second detectors.

10. A device for detecting a radiation signal, comprising:
   a first detector;
   a second detector;
   a first chip on which are arranged the first detector and the second detector;
   a first filter;
   a second filter; and a second chip on which are arranged the first filter and the second filter; wherein:
   the first chip and the second chip are connected to one another in a hermetically sealed fashion, at least one hermetically sealed region being vertically interposed between the first chip and the second chip; and
   the first detector and the second detector are hermetically isolated from each other.

11. The device as recited in claim 10, further comprising:
a self-test mechanism for the device, wherein the self-test mechanism includes at least one heating conductor configured to apply heat to at least one of the first and second detectors.

* * * * *